(12) United States Patent
Shankaranarayanan et al.

(10) Patent No.: US 9,932,287 B2
(45) Date of Patent: Apr. 3, 2018

(54) PROCESS FOR OXIDATION OF ALKYL AROMATIC COMPOUND TO AROMATIC CARBOXYLIC ACID

(71) Applicant: RELIANCE INDUSTRIES LIMITED, Mumbai (IN)

(72) Inventors: Vivek Shankaranarayanan, Hyderabad (IN); Suresh Shantilal Jain, Thane (IN); Pavankumar Aduri, Thane (IN); Rajesh Ratnakar Terdalkar, Thane (IN); Nitin Haribhau Patil, Old Panvel (IN); Parasuveera Uppara, Mumbai (IN)

(73) Assignee: Reliance Industries Limited, Mumbai (IN)

( * ) Notice: Subject to any disclaimer, the term of this patent is extended or adjusted under 35 U.S.C. 154(b) by 68 days.

(21) Appl. No.: 15/117,352

(22) PCT Filed: Feb. 19, 2015

(86) PCT No.: PCT/IB2015/051256
§ 371 (c)(1),
(2) Date: Aug. 8, 2016

(87) PCT Pub. No.: WO2015/125095
PCT Pub. Date: Aug. 27, 2015

(65) Prior Publication Data
US 2016/0347700 A1   Dec. 1, 2016

(30) Foreign Application Priority Data

Feb. 20, 2014   (IN) .......................... 597/MUM/2014

(51) Int. Cl.
*C07C 51/265*   (2006.01)
*C07C 51/43*   (2006.01)
*C07C 51/48*   (2006.01)

(52) U.S. Cl.
CPC ............ *C07C 51/265* (2013.01); *C07C 51/43* (2013.01); *C07C 51/48* (2013.01)

(58) Field of Classification Search
None
See application file for complete search history.

(56) References Cited

U.S. PATENT DOCUMENTS 3,624,145 A    11/1971  Brinn
4,268,690 A    5/1981   Komatsu et al.
2012/0004451 A1  1/2012   Bhattacharyya

*Primary Examiner* — Sudhakar Katakam
*Assistant Examiner* — Jennifer C Sawyer
(74) *Attorney, Agent, or Firm* — Ladas & Parry LLP

(57) ABSTRACT

The present disclosure provides a process for oxidation of p-xylene to terephthalic acid. Recovery of fluid medium and valuable chemicals in carried out using p-xylene as fluid medium which is also the starting material. The recovered stream containing p-xylene, acetic acid and other valuable chemicals is recycled to the oxidation step. The process disclosed in the present disclosure is energy efficient and cost effective.

15 Claims, 1 Drawing Sheet

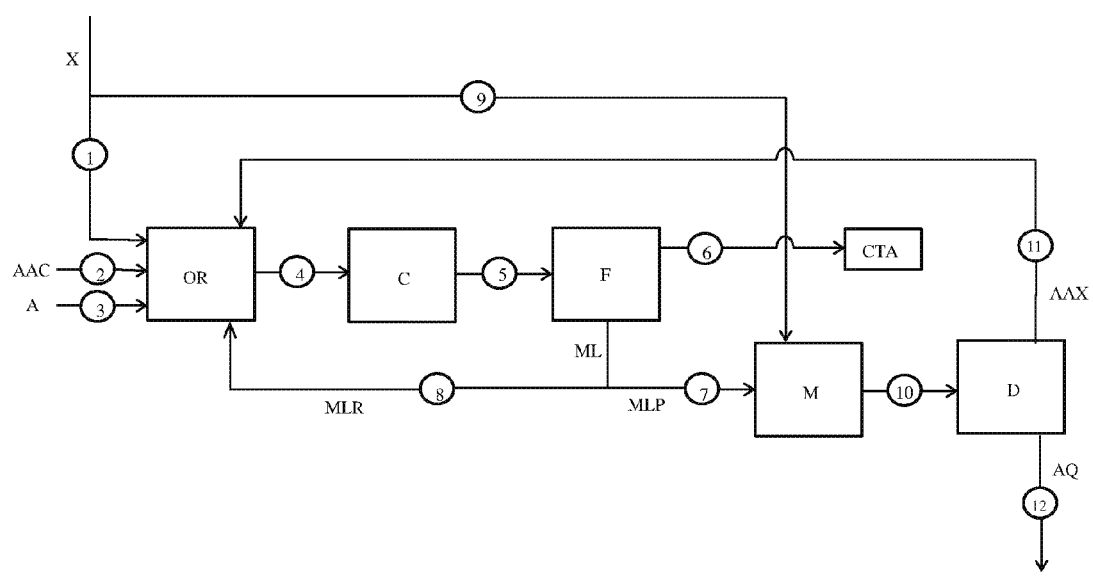

PROCESS FOR OXIDATION OF ALKYL AROMATIC COMPOUND TO AROMATIC CARBOXYLIC ACID

RELATED APPLICATION INFORMATION

This application is a 371 of International Application PCT/IB2015/051256 filed 19 Feb. 2015, which claims priority from India Application No.: 597/MUM/2014 filed 20 Feb. 2014, the content of which is incorporated herein by reference.

FIELD OF THE DISCLOSURE

The present disclosure relates to preparation of aromatic carboxylic acid by oxidation of aromatic alkyl compound. Particularly, the present disclosure relates to a process for recovery of aliphatic carboxylic acid and recycling thereof to aromatic carboxylic acid production process.

BACKGROUND

Terephthalic acid is produced by oxidation of p-xylene in the presence of a catalyst and a promoter in an aliphatic carboxylic acid as a fluid medium. From the process optimization point of view, it is crucial to have the aliphatic carboxylic acid recovered and recycled without affecting the quality of final product.

Terephthalic acid is useful in a variety of industrial applications and chemical processes mainly in polyester field. Terephthalic acid is produced commercially in an oxidation reactor by oxidation of p-xylene using oxygen in acetic acid as a fluid medium, and in the presence of a catalyst and a promoter. Salts of Cobalt, Manganese, Chromium, Copper, Nickel, Vanadium, Iron, Molybdenum, Tin, Cerium, Zirconium, Cesium and Titanium such as acetate or bromide are used as catalyst and organic and inorganic bromide compounds such as hydrobromic acid and ionic liquids containing bromide as anion are used as the promoters in the reaction.

Water is produced during this reaction. Further, other organic compounds like trimellitic acid, 4-carboxybenzaldehyde, p-toluic acid, brominated compounds and the like are produced during the oxidation reaction. Water and these byproducts are present in soluble form in the reaction mixture.

First step of downstream process comprises a series of crystallizers used for crystallizing out terephthalic acid from the reaction mixture. The precipitated terephthalic acid is obtained as a cake. The mother liquor obtained after crystallization contains terephthalic acid, oxidation intermediates of terephthalic acid, other organic chemicals such as side products, byproducts, catalysts and water dissolved in acetic acid.

One byproduct of the oxidation reaction is trimellitic acid. Trimellitic acid, at concentrations above 2000 ppm, forms manganese trimellitate and similar salts with other metals which forms a coat on the filter cloth and affect filtration system performance. The other organic chemicals in this stream include isophthalic acid, o-phthalic acid, benzoic acid, other brominated organic acids, 4-carboxybenzaldehyde, p-toluic acid, salt/s of metal/s. High concentrations of these impurities impact both the quality and the utilization of the plant due to fouling in the vessel and in the circulation heater that requires frequent caustic washes.

For maintaining lower concentration of these organic compounds, the filtrate from the crystallization step is divided into two parts. One part (80-95%) is recycled directly to the oxidation process, whereas, the second stream (5-20%), called the purge stream, is sent for purification before it is recycled. The step of purification involves removal of water and undesired chemicals form the purge stream.

The purge stream is sent to the fluid medium recovery area where it is heated at high temperature and flashed for recovery of acetic acid. High temperature flashing and evaporation is a highly energy intensive process.

After removal of most of the acetic acid, valuable organic chemicals like terephthalic acid, 4-carboxy benzaldehyde, p-toluic acid, benzoic acid and the like are discarded or sold out as low value product. This results in a low yield of terephthalic acid.

To make the process further economical, it is required that the terephthalic acid and oxidation intermediates are sent back to the oxidation reactor. The oxidation intermediates of terephthalic acid will get further oxidized and produce terephthalic acid which will increase yield of the process.

There is, therefore, a need to develop a process for continuous oxidation of p-xylene to terephthalic acid where the fluid medium and valuable chemicals are recovered and recycled in an energy efficient manner. Further, it is desired that the water and trimellitic acid produced during the oxidation are continuously removed.

OBJECTS

Some of the objects of the present disclosure, which at least one embodiment herein satisfies, are as follows:

An object of the present disclosure is to provide a process for continuous oxidation of an alkyl aromatic compound.

Another object of the present disclosure is recovery of an aliphatic carboxylic acid from the process of continuous oxidation of an alkyl aromatic compound in an energy efficient manner.

Another object of the present disclosure is to provide a process for recovery of valuable chemicals with minimum amount of trimellitic acid from the process of continuous oxidation of an alkyl aromatic compound.

Another object of the present disclosure is to provide process for recovery of aliphatic acid and other valuable chemicals by concurrent extraction method, counter current extraction method or a combination thereof.

Another object of the present disclosure is to provide process for recovery of aliphatic acid and other valuable chemicals by single or multiples stage extraction method.

Yet another object of the present disclosure is to provide a process for recycling the recovered aliphatic carboxylic acid and valuable chemicals to process of continuous oxidation of an alkyl aromatic compound.

Other objects and advantages of the present disclosure will be more apparent from the following description when read in conjunction with the accompanying figures, which are not intended to limit the scope of the present disclosure.

SUMMARY

In accordance with one aspect of the present disclosure there is provided a process for the oxidation of p-xylene to terephthalic acid using an oxidizing agent in the presence of metal salt as a catalyst and a promoter in an aliphatic carboxylic acid as a fluid medium.

The fluid medium and valuable chemicals such as the oxidation intermediates of terephthalic acid are recycled to the oxidation process. Trimellitic acid and water produced during oxidation are removed from the reaction mixture. The concentration of trimellitic acid in the reaction mixture is maintained below 2000 ppm to avoid blockage of filtration assembly.

The recovery of the fluid medium and the valuable chemicals as well as the removal of trimellitic acid and water from purge stream is achieved by extraction using p-xylene as an organic fluid medium. The organic phase obtained from the extraction step is recycled directly to oxidation process since p-xylene is the starting material for oxidation.

BRIEF DESCRIPTION OF THE ACCOMPANYING DRAWINGS

The present disclosure will now be described with the help of the accompanying drawings, in which:

FIG. 1 illustrates an exemplary process of the present disclosure where p-xylene (X), catalysts, promoter and fresh acetic acid mixture (AAC) is fed to an oxidation reactor (OR) via lines 1 and 2 respectively. Oxidizing agent (A) is introduced at the bottom of reactor by means of a sparger via line 3. Recycle stream (MLR) and organic stream (AAX) comprising p-xylene, oxidation intermediates of terephthalic acid and acetic acid are fed to the reactor via lines 8 and 11 respectively. The reaction mixture from oxidation reactor is fed to crystallizer (C) by line 4. After crystallization, the reaction mixture is transferred to filtration unit (F) from which crude terephthalic acid (CTA) is obtained as a cake. Mother liquor (ML) from filtration unit (F) is divided into two parts: a recycle stream (MLR) and a purge stream (MLP). Recycle stream (MLR) is recycled back to oxidation reactor section via line 8. The purge stream is sent to mixer (M) for further processing. In the mixer (M), the purge stream is mixed with p-xylene (X) which is supplied via line 9. The mixer can be a single or series of reactor/reactors such as continuous stirred flow reactor, static mixture, plug flow reactor, packed bed extraction column, multiple chamber/compartment agitated extraction column and the like, and combination thereof. The outlet stream from the mixer (M) goes to the decanter (D) via line 10 to separate organic stream (AAX) and aqueous stream (AQ). The organic stream comprising acetic acid, oxidation intermediates of terephthalic acid and p-xylene (AAX) goes to oxidation reactor via line 11. Aqueous stream (AQ) is sent to recovery section for separation of acetic acid, p-xylene, metal salt and other impurities and/or to catalyst recovery section for recovery of catalysts.

FIG. 1 illustrates flow-chart of an exemplary process of the present disclosure.

DETAILED DESCRIPTION

The present disclosure relates to the oxidation of p-xylene to terephthalic acid. The fluid medium and other valuable chemicals in the reaction mixture are recovered by extraction using p-xylene as an organic fluid medium. Since, p-xylene is the starting material, the organic stream obtained from the extraction step can be directly recycled, thereby rendering the overall process economical and energy efficient.

In accordance with one aspect of the present disclosure there is provided a process for the oxidation of p-xylene to terephthalic acid comprising the following steps.

The first step involves oxidizing p-xylene using at least one oxidizing agent in the presence of at least one metal salt as a catalyst and at least one promoter in at least one aliphatic carboxylic acid as a fluid medium to obtain a reaction mixture comprising terephthalic acid, oxidation intermediates of terephthalic acid, trimellitic acid, side products, by products, at least one metal salt, the promoter, the aliphatic carboxylic acid and water. The oxidation intermediates of terephthalic acid comprise at least one compound selected from the group consisting of p-tolualdehyde, p-toluic acid and 4-carboxy benzaldehyde.

The second step involves separating a partial amount of terephthalic acid from the reaction mixture by crystallization and filtration to obtain crude terephthalic acid and a mother liquor. The crude terephthalic acid comprises terephthalic acid and trace amount of intermediates, side products, by products and the metal salt. The mother liquor comprises terephthalic acid, the oxidation intermediates of terephthalic acid, by products, side products, trimellitic acid, the promoter, at least one metal salt and water dissolved in the aliphatic carboxylic acid.

The third step involves dividing the filtrate into a recycle stream and a purge stream. The ratio of the amount of the recycle stream and the purge stream is in the range from 19:1 to 4:1. The recycle stream is recycled to the first step.

In accordance with one embodiment of the present disclosure, the ratio of the amount of the recycle stream and the purge stream is 10:1.

The fourth step involves extracting p-xylene soluble chemicals from the purge stream by adding p-xylene to the purge stream and mixing at a predetermined temperature to obtain a biphasic mixture, which after separation, provides an organic stream and an aqueous stream. The organic stream comprises the aliphatic carboxylic acid, the oxidation intermediates of terephthalic acid and p-xylene, and the aqueous stream comprises the aliphatic carboxylic acid, trimellitic acid, other organic and inorganic chemicals, the promoter and at least one metal salt.

The use of xylene for extracting in process of the present disclosure avoids the contamination which can occur during process modification or intensification.

The fifth step involves recycling the organic stream comprising the aliphatic carboxylic acid, the oxidation intermediates of terephthalic acid and p-xylene to the first step.

The sixth step involves recovering at least one metal salt from the aqueous stream and recycling the recovered metal salt to the first step.

The concentration of trimellitic acid in the reaction mixture is below 2000 ppm. Maintaining the amount of trimellitic acid at this level ensures that the filtration assembly is not adversely affected due to the presence of trimellitic acid in reaction mixture.

The aliphatic carboxylic acid is acetic acid.

The oxidizing agent is selected from the group consisting of air and oxygen.

In accordance with one embodiment of the present disclosure, the oxidizing agent is air.

The metal salt is selected from the group consisting acetate and bromide salts of Cobalt, Manganese, Chromium, Copper, Nickel, Vanadium, Iron, Molybdenum, Tin, Cerium, Zirconium, Cesium and Titanium.

In accordance with one embodiment of the present disclosure, the metal salt is at least one selected from the group consisting of Cobalt acetate, Manganese acetate, Cobalt bromide and Manganese bromide.

The promoter selected from the group consisting of organic bromide compounds and ionic liquid containing bromide as anion.

In accordance with one embodiment of the present disclosure, the promoter is hydrobromic acid.

In accordance with another embodiment of the present disclosure, the promoter is ionic liquids containing bromide as anion. The ionic liquid containing bromide as anion is at least one selected from the group consisting of trihexyltetradecylphosphonium bromide, tetra-n-octylphosphonium bromide, 1-butyl-3-methylimidazolium bromide, 1-hexyl-3-methylimidazoline bromide, 1-butyl-2,3-dimethylimidazolium bromide, 1-methyl-3-octylimidazolium bromide, 1-decyl-3-methylimidazolium bromide, 1-hexadecyl-3-methylimidazolium bromide, 1-methyl-3-octadecylimidazolium bromide, 1,2-dimethyl-3-propylimidazolium bromide, 1-ethyl-3-methylimidazolium bromide, 1-(3-hydroxypropyl)-3-methylimidazolium bromide, N-tributyl-N-methylammonium bromide, N-trimethyl-N-butylammonium bromide, N,N-diethyl-N-methyl-N-propylammonium bromide, N,N-dimethyl-N-ethyl-N-benzyl bromide, N,N-dimethyl-N-ethyl-N-phenylethylammonium bromide, N-ethyl-N-methylpiperidinium bromide, N-propyl-N-methylpiperidinium bromide, N-propyl-N-methylpyrrolidinium bromide, 1-methyl-1-pentylpyrrolidinium bromide, N-butyl-N-methylpyrrolidinium bromide, N-butyl-N-hexylpyrrolidinium bromide and N-butyl-3-methylpyridinium bromide. The ratio of the amount of the purge stream and the amount of p-xylene in the process step of extracting ranges from 1:5 to 2:1.

In accordance with one embodiment of the present disclosure, the ratio of the amount of the purge stream and the amount of p-xylene in the process step of extracting is 1:1.2.

In accordance with another embodiment of the present disclosure, the ratio of the amount of the purge stream and the amount of p-xylene in the process step of extracting is 1:1.5.

The predetermined temperature ranges from 20 to 140° C.

In accordance with one embodiment of the present disclosure, the predetermined temperature is 27° C.

In accordance with another embodiment of the present disclosure, the predetermined temperature is 42° C.

In accordance with yet another embodiment of the present disclosure, the predetermined temperature is 65° C.

The process step of extracting can be carried out using single extraction technique or multiple extraction technique.

In accordance with one embodiment of the present disclosure, the extraction is carried out by single extraction technique.

In accordance with another embodiment of the present disclosure, the extraction is carried out by multiple extraction technique.

The step of extracting can be carried out using concurrent extraction technique and countercurrent extraction technique and combination thereof.

In accordance with one embodiment of the present disclosure, the extraction is carried out in a reactor selected from the group consisting of continuous stirred flow reactor, static mixture reactor, plug flow reactor, packed bed extraction column, multiple chamber/compartment agitated extraction column and the like, and combination thereof.

In accordance with one embodiment of the present disclosure, the extraction is carried out in a single multiple compartment agitated extraction column.

During the process step of extracting, p-xylene partially extracts acetic acid and valuable chemicals from the purge stream.

The amount of the aliphatic carboxylic acid extracted in the organic stream from the purge stream is greater than 20% of the total amount in the purge stream.

The amount of the trimellitic acid extracted in the organic stream from the purge stream is less than 35% of the total amount in the purge stream.

Greater than 65% of the trimellitic acid remains in the aqueous stream and hence gets eliminated from the purge stream. The removal of trimellitic acid from the purge stream helps in maintaining the amount of trimellitic acid below 2000 ppm in the reaction mixture. Maintaining the level of trimellitic acid below 2000 ppm is required for continuous process. If the level of trimellitic acid exceeds 2000 ppm, deposition of salt of trimellitic acid on the filtration media takes place resulting in reduced efficiency of filtration process.

The amount of p-toluic acid extracted in the organic stream from the purge stream is greater than 50% of the total amount in the purge stream.

The amount of 4-carboxybenzaldehyde extracted from the purge stream is greater than 50% of the total amount in the purge stream.

In accordance with one embodiment of the present disclosure, the organic stream after extraction contains 45% of the total acetic acid, 60% 4-carboxybenzaldehyde, 80% p-toluic acid and 23% of the total trimellitic acid present in the purge stream.

In accordance with another embodiment of the present disclosure, the organic stream after extraction contains 50% of total acetic acid, 60% total 4-carboxy benzaldehyde, 80% total p-toluic acid and 22% total trimellitic acid present in the purge stream.

In the sixth step at least one metal salt is recovered from the aqueous stream and the recovered metal salt is recycled to the first step.

In one embodiment of the present disclosure, 75% of cobalt metal salt and 92% of manganese metal salt were recovered from the purge stream and recycled back to the oxidation step.

The oxidation of p-xylene produces terephthalic acid which is isolated from the reaction mixture by crystallization followed by filtration. The mother liquor obtained from the crystallization process contains acetic acid and valuable chemicals. In order to make the overall process economical, acetic acid and the valuable chemicals are recovered and recycled.

The valuable chemicals include oxidation intermediates such as p-toluealdehyde, p-toluic acid and 4-carboxy benzaldehyde which can be further oxidized to terephthalic acid. Recovery and recycle of such products increases the overall yield of terephthalic acid.

The step of extracting is carried out using p-xylene as an organic fluid medium. p-xylene is also the starting material in first step. Hence, the extracted material need not be separated from p-xylene. The organic stream obtained after extraction is directly recycled to the first step.

Trimellitic acid produces trimelletate salts by reacting with metal present in the reaction mixture. Higher amount trimelletate salts of metal have detrimental effect on the functioning of the filtration unit. Thus, the removal of trimellitic acid is helpful for carrying out the oxidation of p-xylene in a continuous manner.

Higher amount of organic compounds in the reaction mixture and subsequent stream leads to deposition of those compounds on the process vessels, circulation heaters and transfer lines. Removal of these organic chemicals reduces or avoids the caustic washes of the vessel and circulation heater that are required in high temperature flashing and evaporation operation owing to their fouling.

Use of the two stage extraction led to recovery of higher amount of acetic acid as compared to single stage extraction. At the same time, less amount of the trimellitic acid is recovered using two stage extraction as compared to single stage extraction. The present disclosure is further described in light of the following examples which are set forth for illustration purpose only and not to be construed for limiting the scope of the disclosure.

EXAMPLES

Example 1

Single stage extraction at 27° C.

100 g of the purge stream (cooled to 27° C.) and 120 g of p-xylene were mixed in a round bottom flask. This mixture was stirred at 27° C. at 1000 rpm for 5 minutes using paddle stirrer. After layer separation, both aqueous (bottom layer) and organic (upper layer of p-xylene) layer were separated and analyzed for acetic acid and other organic acid contents. 45% acetic acid, 60% 4-carboxybenzaldehyde, 80% p-toluic acid and 23% trimellitic acid of initial content in purge stream were extracted into p-xylene layer.

Example 2

Single stage extraction at 42° C.

100 g of the purge stream at 65° C. and 120 g of p-xylene at 27° C. were mixed in a round bottom flask and stirred at 300 rpm for 5 minutes using paddle stirrer to obtain a mixture at 42° C., which was maintained till layers separated. After layer separation, both aqueous (bottom layer) and organic (upper layer of p-xylene) layer were analyzed for acetic acid and other organic acid contents. 58% acetic acid, 69% 4-carboxybenzaldehyde, 85% p-toluic acid and 26% trimellitic acid of initial content in second stream were extracted into p-xylene layer.

Example 3

Single stage extraction at 65° C.

100 g of the purge stream and 120 g of p-xylene were mixed to obtain a mixture at 65° C. This mixture was stirred at 1000 rpm for 5 minutes using paddle stirrer. After layer separation, both aqueous (bottom layer) and organic (upper layer of p-xylene) layer were analyzed for acetic acid and other organic acid contents. 65% acetic acid, 79% terephthalic acid, 86% 4-carboxy benzaldehyde, 88% p-toluic acid and 29% trimellitic acid of initial content in the purge stream were extracted into p-xylene layer.

Thus, at higher temperature, higher amounts of acetic acid and trimellitic acid are extracted.

Example 4

Two stage extraction at 27° C.

Experimental conditions are similar to example-1 except that p-xylene was used in two stages.

In first stage, 100 g of purge stream and 60 g of p-xylene were mixed a round bottom flask. 90 g of organic phase and 70 g of aqueous phase were obtained after layer separation. Organic (p-xylene) layer of stage-1 was analyzed for acetic acid and other organic acid contents.

In the second stage, 70 g of the aqueous layer obtained from stage-1 was treated with 60 g of p-xylene under similar experimental conditions. 92 g of p-xylene layer and 47 g of aqueous layer were obtained after layer separation.

60% Acetic acid, 70% 4-carboxybenzaldehyde, 85% p-toluic acid and 22% trimellitic acid of initial content in purge stream were extracted into p-xylene layer.

Thus, use of the two stage extraction led to recovery of higher amount of acetic acid as compared to single stage extraction. At the same time, less amount of the trimellitic acid is recovered using two stage extraction as compared to single stage extraction.

Example 5

Single stage extraction at industrial level

1070 Liters/h of the purge stream (MLP) and 1600 liters/h of p-xylene (9) were sent to a continuous flow stirred tank reactor (M) of capacity 30 liters operating at 27° C. and 60 rpm. The outlet stream (10) of 2670 liters/h was sent to a continuous decanter (D) of capacity 80 liters to separate organic and aqueous stream as first extract (AAX) and first raffinate (AQ) respectively. A continuous separation of 2065 liters/h of first extract stream (AAX) and 605 liters/h of first raffinate stream (AQ) were obtained. In first extract stream (AAX), 50% acetic acid, 60% 4-carboxy benzaldehyde, 80% p-toluic acid and 22% trimellitic acid of their initial content in the purge stream (MLP) were extracted. Extraction of the metal salts and the promoter to first extract phase (AAX) was 1% and 5% of their initial content in the purge stream.

605 liters/h of first raffinate stream (AQ) was sent for the recovery of metal salts. 75% of cobalt and 92% of manganese metal catalysts of its initial content in the purge stream were recovered and recycled back to the oxidation reactor.

Economical Significance and Technical and Advancement

The technical advancements offered by the present disclosure include the realization of:

- The process of the present disclosure provides continuous process for oxidation of p-xylene to terephthalic acid.
- The process of the present disclosure provides recovery of valuable chemicals from the purge stream in oxidation of p-xylene to terephthalic acid.
- The process of the present disclosure provides energy efficient recovery of acetic acid and other chemicals using the extraction process instead of high temperature heating and flashing operation.
- The process of the present disclosure recycles the organic stream from extraction operation directly to oxidation reactor.
- The process of the present disclosure avoids/ reduces the caustic washes of the vessel and circulation heater that are required during high temperature flashing and evaporation operation owing to their fouling.
- The use of the process of the present disclosure avoids the contamination which can occur during process modification/intensification since p-xylene is used for extraction which is starting material for the oxidation step.
- Removal of major amount of trimellitic acid helps in the filtration system performance.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for the oxidation of p-xylene to terephthalic acid comprising the following steps:
   a) oxidizing p-xylene using at least one oxidizing agent in the presence of at least one metal salt as a catalyst and at least one promoter in at least one aliphatic carboxylic acid as a fluid medium to obtain a reaction mixture comprising terephthalic acid, oxidation intermediates of terephthalic acid, trimellitic acid, at least one metal salt, the promoter, the aliphatic carboxylic acid and water; wherein the oxidation intermediates of terephthalic acid comprise at least one compound selected from the group consisting of p-tolualdehyde, p-toluic acid and 4-carboxy benzaldehyde;
   b) separating a partial amount of the terephthalic acid from the reaction mixture by crystallization and filtration to obtain crude terephthalic acid and a mother liquor; wherein the mother liquor comprises trimellitic acid, the promoter, at least one metal salt, water and the aliphatic carboxylic acid;
   c) dividing the mother liquor into a recycle stream and a purge stream; wherein the ratio of the amount of the recycle stream and the purge stream is in the range from 19:1 to 4:1; and recycling the recycle stream to step (a);
   d) extracting p-xylene soluble chemicals from the purge stream by adding p-xylene to the purge stream and mixing at a predetermined temperature to obtain a biphasic mixture, which after separation, provides an organic stream and an aqueous stream; wherein the organic stream comprises p-xylene, the aliphatic carboxylic acid and the oxidation intermediates of terephthalic acid, and the aqueous stream comprises the aliphatic carboxylic acid, trimellitic acid, the promoter and at least one metal salt;
   e) recycling the organic stream comprising p-xylene, the aliphatic carboxylic acid and the oxidation intermediates of terephthalic acid to step (a); and
   f) recovering at least one metal salt from the aqueous stream and recycling the recovered metal salt to step (a);
   wherein, the concentration of trimellitic acid in the reaction mixture is below 2000 ppm.

2. The process as claimed in claim 1, wherein the aliphatic carboxylic acid is acetic acid.

3. The process as claimed in claim 1, wherein the oxidizing agent is selected from the group consisting of air and oxygen.

4. The process as claimed in claim 1, wherein the metal salt is selected from the group consisting acetate and bromide salts of Cobalt, Manganese, Chromium, Copper, Nickel, Vanadium, Iron, Molybdenum, Tin, Cerium, Zirconium, Cesium and Titanium.

5. The process as claimed in claim 1, wherein the metal salt is selected from the group consisting of Cobalt acetate, Manganese acetate, Cobalt bromide and Manganese bromide.

6. The process as claimed in claim 1, wherein promoter is selected from the group consisting of organic bromide compounds and ionic liquid containing bromide as anion.

7. The process as claimed in claim 1, wherein the promoter is an ionic liquid containing bromide as anion selected from the group consisting of trihexyltetradecylphosphonium bromide, tetra-n-octylphosphonium bromide, 1-butyl-3-methylimidazolium bromide, 1-hexyl-3-methylimidazolium bromide, 1-butyl-2,3-dimethylimidazolium bromide, 1-methyl-3-octylimidazolium bromide, 1-decyl-3-methylimidazolium bromide, 1-hexadecyl-3-methylimidazolium bromide, 1-methyl-3-octadecylimidazolium bromide, 1,2-dimethyl-3-propylimidazolium bromide, 1-ethyl-3-methylimidazolium bromide, 1-(3-hydroxypropyl)-3-methylimidazolium bromide, N-tributyl-N-methylammonium bromide, N-trimethyl-N-butylammonium bromide, N,N-diethyl-N-methyl-N-propylammonium bromide, N,N-dimethyl-N-ethyl-N-benzyl bromide, N,N-dimethyl-N-ethyl-N-phenylethylammonium bromide, N-ethyl-N-methylpiperidinium bromide, N-propyl-N-methylpiperidinium bromide, N-propyl-N-methylpyrrolidinium bromide, 1-methyl-1-pentylpyrrolidinium bromide, N-butyl-N-methylpyrrolidinium bromide, N-butyl-N-hexylpyrrolidinium bromide and N-butyl-3-methylpyridinium bromide.

8. The process as claimed in claim 1, wherein the ratio of the amount of the purge stream and the amount of p-xylene in the process step (d) ranges from 1:5 to 2:1.

9. The process as claimed in claim 1, wherein the predetermined temperature of the process step (d) ranges from 20 to 140° C.

10. The process as claimed in claim 1, wherein optionally the step of extracting is carried out using multiple extraction technique.

11. The process as claimed in claim 1, wherein optionally the step of extracting is carried out using concurrent extraction technique, countercurrent extraction technique and combination thereof.

12. The process as claimed in claim 1, wherein optionally the step of extracting is carried out in at least one reactor selected from the group consisting of continuous stirred flow reactor, static mixture reactor, plug flow reactor, packed bed extraction column and multiple compartment agitated extraction column.

13. The process as claimed in claim 1, wherein the amount of the aliphatic carboxylic acid extracted in the organic stream is greater than 20% of the total amount in the purge stream.

14. The process as claimed in claim 1, wherein the amount of trimellitic acid extracted in the organic stream is less than 35% of the total amount in purge stream.

15. The process as claimed in claim 1, wherein the amount of p-toluic acid extracted in the organic stream is greater than 50% of the total amount in the purge stream and the amount of 4-carboxybenzaldehyde extracted in the organic stream is greater than 50% of the total amount in the purge stream.

* * * * *